United States Patent
Lebov et al.

(10) Patent No.: US 11,344,223 B2
(45) Date of Patent: May 31, 2022

(54) METHOD AND AN APPARATUS FOR MEASURING ACETONE CONCENTRATIONS IN BREATH

(71) Applicants: Slava Lebov, Richmond Hill (CA); Sergey Babichenko, Tallinn (EE); Alexander Dudelzak, Ottawa (CA); Aleksei Kuznetsov, Tallinn (EE); Innokenti Sobolev, Maardu (EE); Leino Vint, Harju maakond (EE)

(72) Inventors: Slava Lebov, Richmond Hill (CA); Sergey Babichenko, Tallinn (EE); Alexander Dudelzak, Ottawa (CA); Aleksei Kuznetsov, Tallinn (EE); Innokenti Sobolev, Maardu (EE); Leino Vint, Harju maakond (EE)

(73) Assignee: Solvax Systems Inc.

( * ) Notice: Subject to any disclaimer, the term of this patent is extended or adjusted under 35 U.S.C. 154(b) by 0 days.

(21) Appl. No.: 17/022,505

(22) Filed: Sep. 16, 2020

(65) Prior Publication Data

US 2022/0079469 A1 Mar. 17, 2022

(51) Int. Cl.
- A61B 5/08 (2006.01)
- A61B 5/097 (2006.01)
- G01N 33/497 (2006.01)
- A61B 5/00 (2006.01)

(52) U.S. Cl.
CPC ............ A61B 5/082 (2013.01); A61B 5/0071 (2013.01); A61B 5/097 (2013.01); G01N 33/497 (2013.01); *A61B 2560/0219* (2013.01); *G01N 2033/4975* (2013.01)

(58) Field of Classification Search
CPC ....... A61B 5/082; A61B 5/0071; A61B 5/097; G01N 33/497; G01N 2033/4975
See application file for complete search history.

(56) References Cited

U.S. PATENT DOCUMENTS

| | | | |
|---|---|---|---|
| 2005/0084921 A1* | 4/2005 | Cranley | C12P 7/04 435/25 |
| 2007/0229818 A1 | 10/2007 | Duan et al. | |
| 2015/0289782 A1 | 10/2015 | Peverall et al. | |
| 2016/0054294 A1* | 2/2016 | Rihani | G01N 21/05 73/23.3 |
| 2017/0115272 A1 | 4/2017 | Rihani et al. | |
| 2017/0131260 A1 | 5/2017 | Priefer et al. | |
| 2018/0246036 A1 | 8/2018 | Carty et al. | |

FOREIGN PATENT DOCUMENTS

| | | |
|---|---|---|
| RU | 2547893 C1 | 4/2015 |
| WO | 2015159280 A1 | 10/2015 |

* cited by examiner

*Primary Examiner* — Puya Agahi
(74) *Attorney, Agent, or Firm* — McDonnell Boehnen Hulbert & Berghoff LLP

(57) ABSTRACT

The present invention relates to a method and device for measuring acetone concentrations in breath. Measuring acetone concentrations is based on changes the spectral properties of the fluorophore caused by the chemical interaction of a specific fluorophore with the exhaled air containing acetone which.

7 Claims, 5 Drawing Sheets

METHOD AND AN APPARATUS FOR MEASURING ACETONE CONCENTRATIONS IN BREATH

FIELD OF THE INVENTION

The present invention relates to a method and apparatus for measuring acetone concentrations in breath. In particular, to a method and apparatus based on chemical interaction of a specific fluorophore with the exhaled air containing acetone which changes the spectral properties of the fluorophore.

BACKGROUND OF THE INVENTION

Many optical methods for the detection of acetone in breath, as well as measurement devices made for that purpose, are known in the prior art. See, for example, US20170115272, US20180246036, US20070229818, US20150289782, WO2015159280 and US20170131260 (granted as U.S. Pat. No. 9,921,209).

RU2547893 teaches a method for determining the acetone in the gas phase which utilizes a xerogel matrix containing Nile Red. The presence of acetone vapor hydrogen results in the reversible competitive formation of hydrogen bonds between molecules of acetone and xerogel matrix and the breaking of hydrogen bounds between the xerogel matrix and Nile Red. The breaking hydrogen bonds with a molecule Nile Red is accompanied by a significant increase in fluorescence intensity. The concurrent bonding re-distribution reactions take time and as such the detection process is not immediate. In particular, while the abstract and description state that a 5 minute time period for measurements. Exemplary measurements (see FIG. 2) take significantly longer than 5 minutes (i.e. 1200 seconds which is 20 minutes). The method of RU2547893 allows detecting acetone only at its vapour saturation partial pressure i.e. concentrations of thousands of ppm and higher. Measuring concentrations in the range of 0.5-2.0 ppm characteristic of human exhale would take much longer, perhaps hours and therefore is not a practical method to measure acetone in human exhale. The measurement time and analytical uncertainty may also be impacted by the speed of acetone diffusion in the xerogel pores, which depends on the efficiency of purging air from the pores as well as on other uncontrollable external factors such as ambient temperature, pressure, humidity, etc. As the concurrent reaction of the hydrogen-type bonding in the xerogel-Nile Red-acetone tripartite structure requires saturating xerogel with acetone, the method sensitivity is defined by the acetone concentration exceeding the saturation threshold. This substantially limits the method's sensitivity. Moreover, the Nile Red-xerogel compound based on hydrogen-type bonding does not allow for complete chemical structure restoration enabling repetitive measurements. Such restoration requires high-temperature annealing of the compound, preferably in vacuum. Not only is this impractical; the process also leads to decomposition of Red Nile and breaking its bonding with xerogel.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide a method and an apparatus for measuring acetone concentrations in breath. In accordance with an aspect of the present invention, there is provided a method of measuring acetone in a subject's breath, said method comprises obtaining a sample of the subject's breath; combining said sample with a fluorophore that exhibits a change in fluorophore spectral properties upon interaction of acetone and thereby allowing any acetone in said sample to interact with said fluorophore; and determining an amount of acetone in said sample based on alteration of spectral properties of said fluorophore.

In accordance with another aspect of the invention there is provided a device for measuring acetone in human exhale. the device comprising a means to introduce human exhale fluidly connected to reaction chamber comprising a fluorophore capable of interacting with acetone; one or more light sources capable of illuminating the to induce fluorescence of the said fluorophore; one or more spectral detector(s) capable of detecting fluorescence from said fluorophore and a means for controlling operation of the device and for processing the fluorescence data to derive an acetone concentration.

In accordance with another aspect of the invention, there is provided an insert comprising fluorophore immobilized on the surface of a substrate.

In accordance with another aspect of the invention, there is provided a device for measuring acetone in human exhale. the device comprising a means to introduce human exhale fluidly connected to reaction chamber comprising the insert comprising fluorophore immobilized on the surface of a substrate; one or more light sources capable of illuminating the to induce fluorescence of the said fluorophore; one or more spectral detector(s) capable of detecting fluorescence from said fluorophore and a means for controlling operation of the device and for processing the fluorescence data to derive an acetone concentration.

BRIEF DESCRIPTION OF THE DRAWINGS

These and other features of the invention will become more apparent in the following detailed description in which reference is made to the appended drawings.

DETAILED DESCRIPTION OF THE INVENTION

Figure 1:
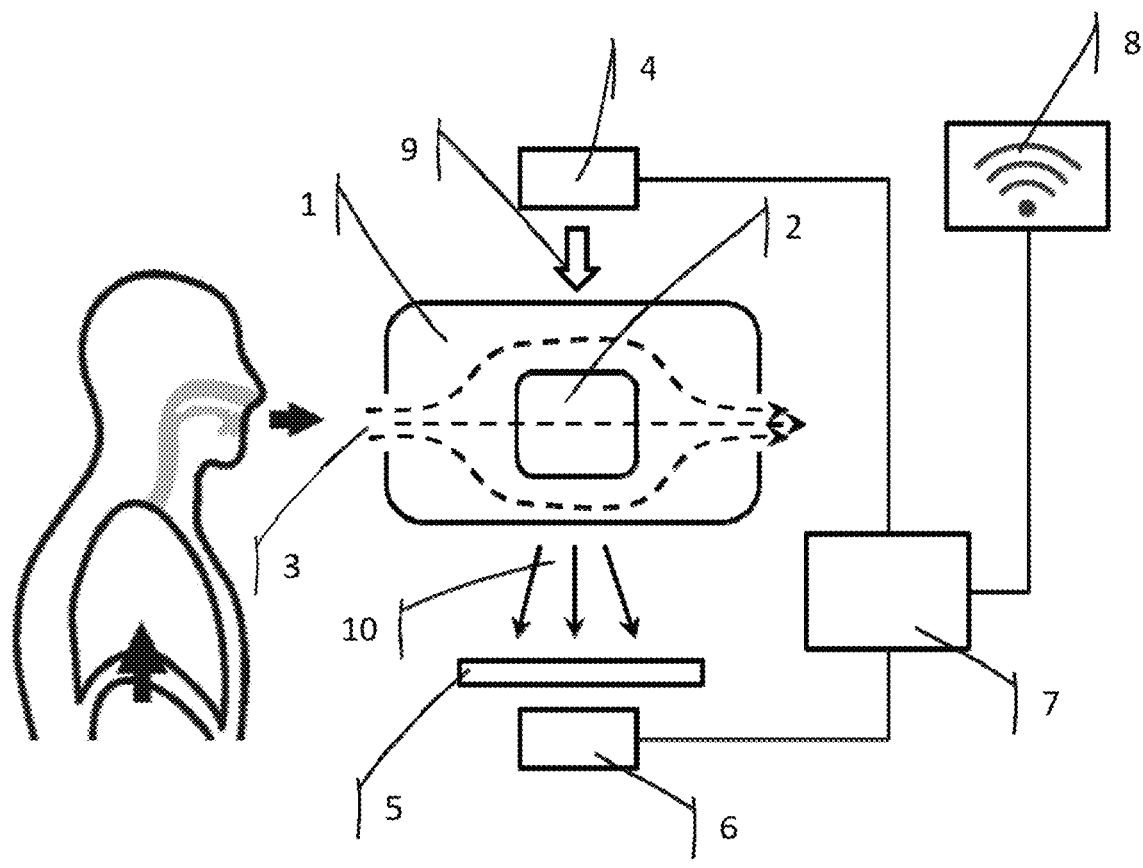
FIG. 1 provides a block diagram of the use of the device of an embodiment of the present invention. (1) reaction volume; (2) assay substrate; (3) inlet airflow; (4) light source; (5) spectral selector; (6) optical detector; (7) microcontroller; (8) communication means; (9) excitation light; (10) fluorescence flux

The invention is based on the changes that occur to the spectral properties of select fluorophores upon interaction acetone. These changes in spectral properties of the fluorophore are proportional to the acetone concentration and can be detected. Accordingly, the invention provides a method and device of detecting acetone in human exhale.

Method

The present invention provides a method of measuring acetone in breath. The method comprises obtaining a sample of a subject's breath; combining said sample with a fluorophore and thereby allowing any acetone in said sample to interact with said fluorophore; and determining an amount of acetone in said sample based on alteration of spectral properties of said fluorophore.

In certain embodiments, a single breath sample is obtained. The measurement procedure may be repeated several times to improve the measurement accuracy. Accordingly, in other embodiments, multiple breath samples are obtained. In certain embodiments where multiple breath samples are obtained, the fluorescence spectra is determined for each breath sample and then integrated to determine concentration in breath, Obtaining a Sample of a Breath Sample.

A breath sample may be obtained by having the subject to be tested exhale or blow into a collection device inlet or an inlet of an acetone measurement device. In certain embodiments, an acetone measurement device is provided and the subject to be tested blows or exhales a breath sample directly into the acetone measurement device.

In certain embodiments, no sample preparation is required prior to combining the breath sample with the fluorophore.

Combining Said Sample with a Fluorophore and Thereby Allowing any Acetone in Said Sample to Interact with Said Fluorophore;

The breath sample is then combined with a fluorophore and any acetone in the sample interacts with the fluorophore and thereby cause changes in the spectral properties of said fluorophore if acetone is present.

The fluorophore may be any fluorophore that exhibits a change in fluorophore spectral properties upon interaction of acetone. The change in spectral properties may include change in the spectral shape and/or the intensity of fluorescence. In certain embodiments, these interactions and alteration of the spectral properties is reversible. Non-limiting examples of fluorophores include Nile Red, Badan (6-Bromoacetyl-2-Dimethylaminonaphthalene), Prodan (1-[6-(dimethylamino)naphthalen-2-yl]propan-1-one), Laurdan (6-Dodecanoyl-N,N-dimethyl-2-naphthylamine), and derivatives thereof. In certain embodiments, the fluorophore is Nile Red.

In certain embodiments, the fluorophore is immobilized on the surface of a substrate. The substrate may be any substrate that does not impact fluorescence. For example, the substrate does not prevent the transmission of the light used to excite the fluorescent protein and does not impact the spectral properties of the fluorescent protein. In certain embodiments, the substrate is also chemically inert towards the fluorophore and the acetone. In other words, the acetone being detected interacts chemically only with the fluorophore not with the substrate, and the detection does not require involving any intermediate reactions of acetone with anything else other than the fluorophore. This direct interaction may reduce assay time and/or may enhance assay sensitivity.

Exemplary substrates include but are not limited to fused silica, quartz, PMMA, polyethylene, fluoride-doped polyethylene or PMMA, certain optical glasses and silica gels. In certain embodiments, the substrate is fused silica.

Determining an Amount of Acetone in Said Sample Based on Alteration of Spectral Properties of Said Fluorophore.

The amount of acetone in the breath sample is based on alteration of spectral properties of said fluorophore. The alteration of spectral properties may be determined by comparing the fluorescence spectrum measured in the presence of the sample with a reference of the fluorescence spectrum shape and intensity. The reference may be the known fluorescence spectrum of the fluorophore. In certain embodiments, the reference is a baseline fluorescence measured prior to obtaining the breath sample. By obtaining a baseline fluorescence just prior to obtaining the sample, any acetone in the ambient air will be accounted for.

A worker skilled in the art would readily appreciate that the fluorophore must be illuminated in order for the fluorophore to fluoresce. Accordingly, the method comprises illuminating the fluorophore with the appropriate wavelengths of light and measuring the resulting fluorescence. In certain embodiments, visible light is used for illumination. In certain embodiments, the light source is one or more LEDs.

A worker skilled in the art would readily appreciate that one or more spectral detector(s) capable of detecting fluorescence from said fluorophore. Accordingly, the method comprises measuring fluorescence with one or more spectral detector(s).

The amount of acetone in a sample may be determined by comparing the measured fluorescence with a reference which relates fluorescence spectrum of the fluorophore with concentrations of acetone. In certain embodiments there is a calibration curve relating concentration of acetone to fluorescence intensity.

Acetone levels may be used to monitor a number of health conditions. For example, acetone is found in the breath of diabetics and has been shown to correlate with blood-glucose levels. Breath acetone is a reliable indicator of ketosis in adults consuming ketogenic meals. Accordingly, in certain embodiments, the methods further comprise determining a physiological parameter based at least in part on the determined amount of acetone. In specific embodiments, the physiological parameter is a blood sugar level.

Device

The invention also relates to a device for measuring acetone in human exhale. In certain embodiments, the device is capable of measuring sub-ppm levels of acetone in breath. The device may be hand-held. The device may be single use or reusable.

The device comprises a means to introduce human exhale fluidly connected to reaction chamber comprising a fluorophore capable of interacting with acetone; one or more light sources capable of illuminating the fluorophore to induce fluorescence of the said fluorophore; and one or more spectral detector(s) capable of detecting fluorescence from said fluorophore.

The means to introduce human exhale (inlet) may comprise a tube or a mouth piece which allows a person to exhale into or blow into the device and is fluidly connected to the reaction chamber. In certain embodiments, the means to introduce human exhale also allows for two-way airflow and as such allows for the exhale to exit the device following testing. In certain embodiments, the means to introduce human exhale to configured to allow for one-way airflow. In such embodiments, the device may also comprise an outlet in fluid communication with the reaction chamber which allows human exhale to exit the device. In certain embodiments, the outlet is configured to allow for one-way airflow.

In certain embodiments, the device is configured such that the inlet, reaction chamber and outlet are in series such that airflow travels into the inlet through the reaction chamber and out the outlet.

The reaction chamber comprises a fluorophore capable of interacting with acetone or is configured to receive an assay insert comprising a fluorophore. In certain embodiments, the reaction chamber comprises one or more assay inserts comprising the fluorophore immobilized on the surface of a substrate. The fluorophore may be any fluorophore that exhibits a change in fluorophore spectral properties, including change in the spectral shape and/or the intensity of fluorescence upon interaction of acetone. Non-limiting examples of fluorophores include Nile Red, Badan (6-Bromoacetyl-2-Dimethylaminonaphthalene), Prodan (1-[6-(dimethylamino)naphthalen-2-yl]propan-1-one), Laurdan (6-Dodecanoyl-N,N-dimethyl-2-naphthylamine), and derivatives thereof. In certain embodiments, the fluorophore is Nile Red. The substrate may be any substrate that does not impact fluorescence. Exemplary substrates include but are not limited to fused silica, quartz, PMMA, polyethylene, fluoride-doped polyethylene or PMMA, certain optical glasses and silica gels. In certain embodiments, the substrate is fused silica.

Methods of immobilizing the fluorophore to the surface are known in the art and will be dependent on the fluorophore and the substrate. In certain embodiments, the fluorophore is immobilized as a monolayer on the substrate surface by covalent linkage to provide homogeneous distribution of fluorophore over the assay substrate. In certain embodiments, a linker is used to immobilize the fluorophore to the substrate. A number of organic compounds selected in accordance with the substrate type—e.g. aliphatic or aromatic complexes with carboxyl or amino groups—can be used as such linkers.

In certain embodiments, a coating comprising the fluorophore coats the substrate. Accordingly, in certain embodiments, the assay insert comprises a functionalized layer which comes in contact with the breath sample and comprises fluorophores and a substrate layer supporting the functionalized layer. The coating may be a variety of coatings so long as it does not impact fluorescence. For example, does not prevent the transmission of the light used to excite the fluorescent protein and does not impact the spectral properties of the fluorescent protein. In certain embodiments, the substrate is also chemically inert towards the fluorophore and the acetone. In specific embodiments, the coating is a polymer. In such embodiments, the fluorophore may be dissolved in the polymer in a specific amount and then the polymer containing the fluorophore coated on the substrate provide a preset concentration of fluorophore.

In certain embodiments, the insert comprises an external layer over the functionalized layer which minimizes the influence of other exhale components on the measurement results.

To make such an outer layer, various chemical compounds which are hydrophobic and have an active group/complex enabling immobilization reactions. Exemplary compounds include but are not limited to carbonic acids with aliphatic chains i.e. saturated fatty acids such as Hexanoic acid, Octanoic acid, Dodecanoic acid, etc. and unsaturated fatty acids such as Merystoleic acid, Palmitoleic acid, etc.).

Accordingly, in certain embodiments, the assay insert comprises an external layer to minimize influence of other exhale components, a functionalized layer comprising fluorophores and a substrate layer.

The assay insert may be either a single use or multiple uses. The assay insert may be non-removable or removable. In embodiments, where the insert is removable, the present invention provides replacement inserts. In certain embodiments where the assay insert is removable, the insert must be inserted prior to use. The insert may be various shapes including but not limited to plates, spheres or other spatial structures. The device sensitivity for the detection of acetone may be increased by enlarging the reaction surface area of the assay insert. In certain embodiments, surface area is increased by utilizing a porous—mesh, fiber, etc.—structure. In certain embodiments, device sensitivity may be increased by utilizing more than one assay insert.

The device further comprises one or more light sources capable of illuminating the fluorophore to induce fluorescence of the said fluorophore. Accordingly, the light source is capable of producing light having the spectral width fitting the excitation spectrum of fluorophore interacting with acetone to induce the fluorophore fluorescence. In certain embodiments, the light source produces visible light. In certain embodiments, the one or more light sources is Light Emitting Diode (LED)(s).

The device further comprises one or more spectral detector(s) capable of detecting fluorescence from said fluorophore. In certain embodiments, the one or more spectral detector(s) is a photodiode having an optical filter with the spectral width chosen to select the excitation light allowing the fluorophore fluorescence to interact with acetone and be further passed to photodetector in order to detect and record the fluorescence intensity. In other embodiments, the spectral detector consists of several discrete photodiodes coupled with compatible optical filters. In other embodiments, the spectral detector is a linear array or a matrix of miniature photoreceivers coupled with a spectrally dispersive unit—a spectrometer, a monolithic or integrated dispersive/spectrally selective block, etc.—splitting the fluorescence into discrete spectral bands at various wavelength peaks to provide simultaneous multichannel measurements of the spectral shape of said fluorescence. Optionally, the dispersive/spectrally selective block comprises of an array of various optical spectral filters in front of the detector. Optionally, the spectrally dispersive unit utilizes—one at the time—any optical dispersive elements such as diffraction gratings, prisms, interference etalons or alike.

The device further comprises a means for controlling operation of the device and for processing the fluorescence data to derive an acetone concentration and optionally other physiological parameters. The device may further comprise a means for communicating the measured acetone concentration values. Means for communicating the measured acetone values may include a digital display and/or communications system that capable of communicating with a remotely located device, such as a cellphone. In certain embodiments, the device is Wifi, Bluetooth and/or cellular enabled. The device may further comprise a data storage means capable of storing collected data and/or derived acetone concentrations.

In certain embodiments, the operations of the device is controlled with a built-in integrated microcontroller based on the embedded signal and data processing software providing for the detector signal readout, integrating it over time, deriving the acetone concentration, reporting measurement results to the visualization, display and storage facilities, etc. as necessary.

EXAMPLE

With reference to the figures, a non-limiting usage example is described below.

Figure 2:
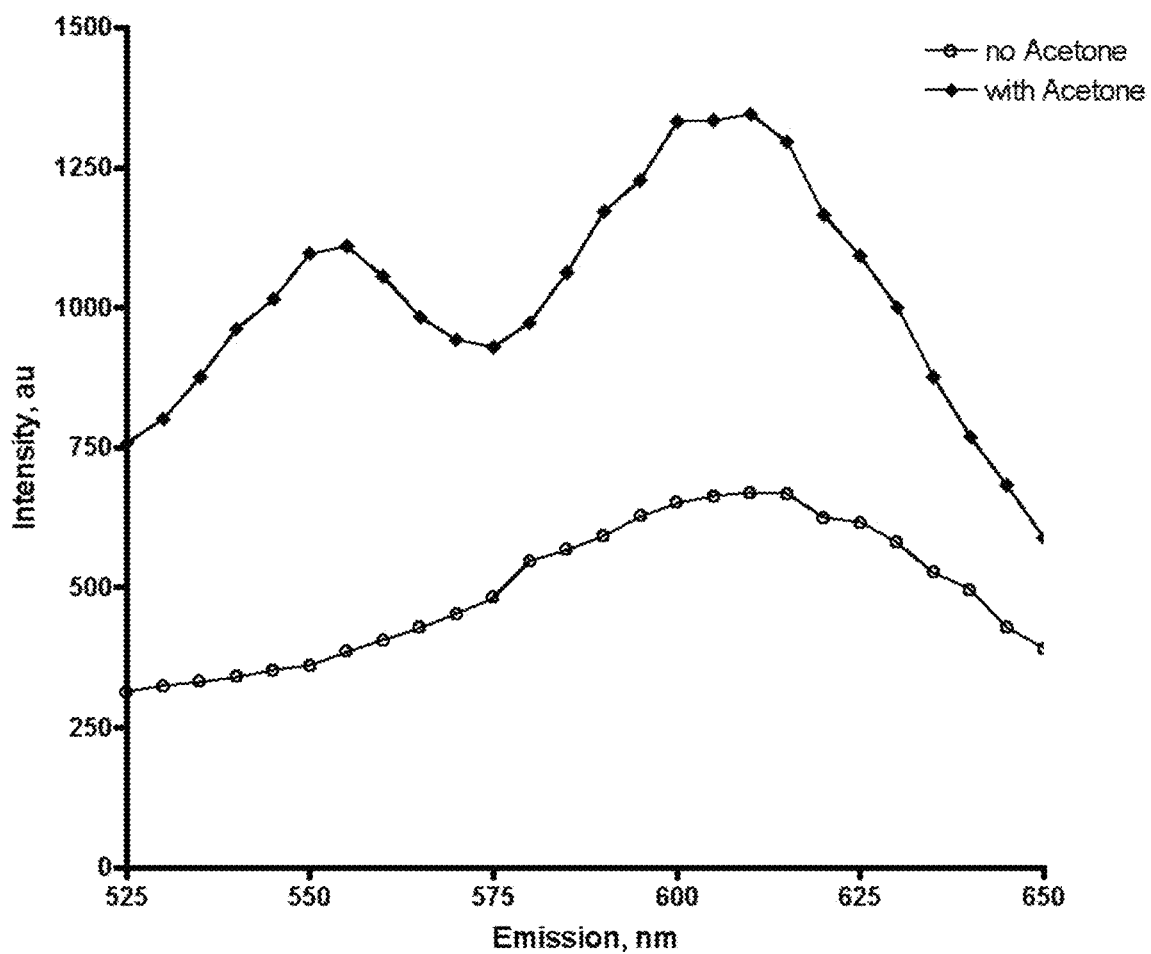
FIG. 2 illustrates the fluorescence spectra of the Nile Red dye.

A reaction volume of 200 ml (1 in FIG. 1) with the exhaled air inflow and outflow tubes contains the assay substrate (2). The substrate (2) is made of the optically transparent PVA film coated by a thin layer of a polymer with the embedded Nile Red dye at the concentration of 10

μg/ml. A 30 mW power LED (3) emitting at the wavelength of 530 nm serves as a light source. The spectral detector (3) is made of a pair of photodiodes coupled with the bandpass filters having maximum transmission at the wavelength of 555 nm (channel 1) and 615 nm (channel 2). These channels' spectral positions match the fluorescence peaks of the Nile Red dye interacted and not interacted with acetone correspondingly (FIG. 2).

Figure 3:
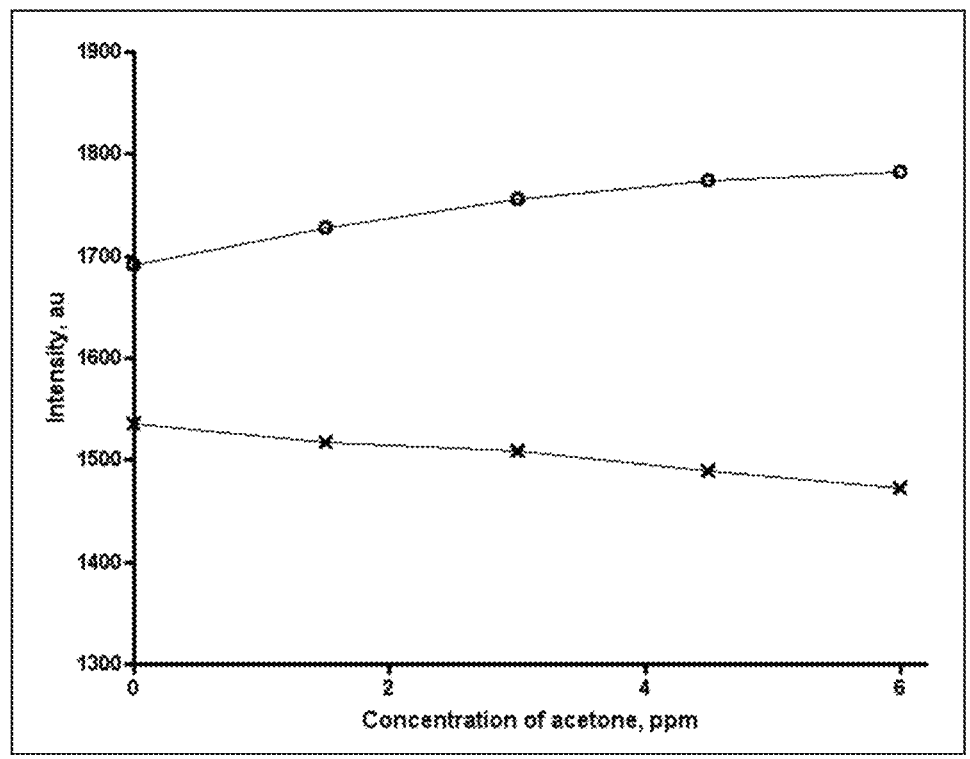
FIG. 3 illustrates fluorescence intensity of the Nile Red dye at the emission wavelength of 555 nm (crosses), and 615 nm (circles) vs. concentrations of acetone added to the fixed air volume.
Figure 4:
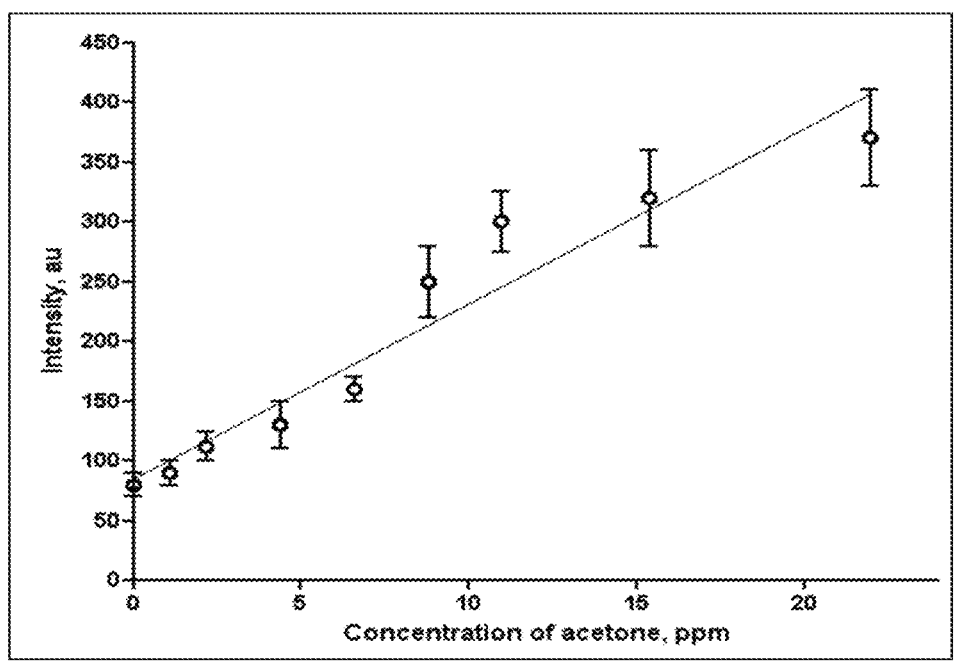
FIG. 4 illustrates the fluorescence intensity of the Nile Red dye increases with acetone concentration in the exhale.

Due to the interaction with acetone, fluorescence intensity in the channel 2 is increased, and the fluorescence intensity in channel 1 is decreased. Such changes are the greater the higher concentrations of acetone is in the air (FIG. 3). This is indicated by changes in the spectral shape of the Nile Red fluorescence resulting from interactions with acetone. The proportion of the spectral intensity variation affected by the acetone concentration is used to make the calibration curve (FIG. 4) for deriving the concentration of acetone from the relative change of the corresponding fluorescence intensity of the assay substrate.

Figure 5:
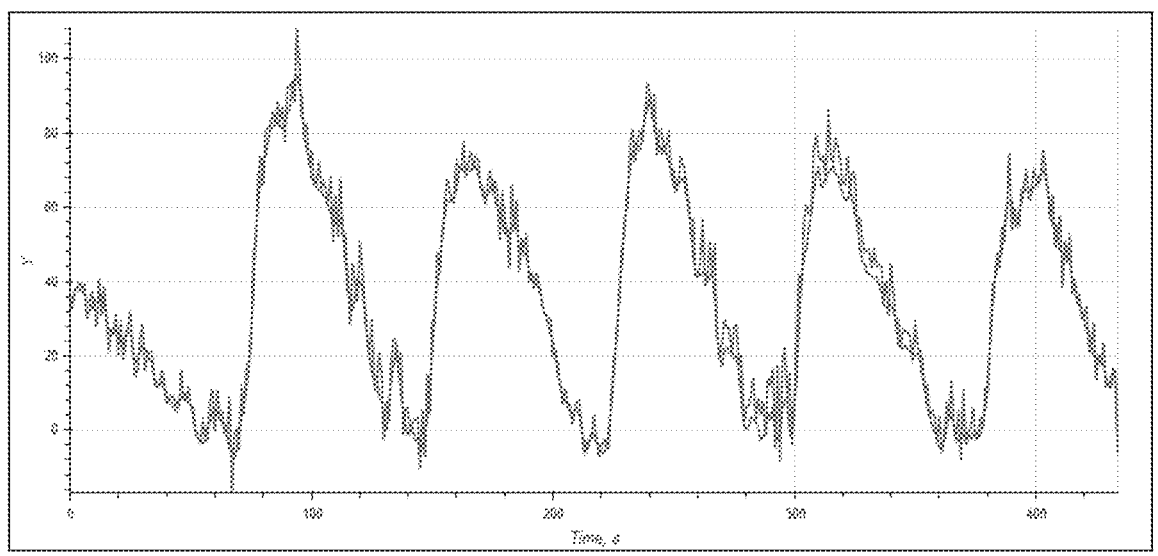
FIG. 5 illustrates the fluorescence signal of sequential exhales through the reaction volume vs. time

The repeated exhales reproduce the dynamics of detector signal in time (FIG. 5) thus allowing reliable measurement of acetone concentrations in human exhale.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims.

We claim:

1. A method of measuring acetone in a subject's breath, said method comprises obtaining a sample of the subject's breath; combining said sample with a fluorophore that exhibits a change in fluorophore spectral properties upon interaction with acetone and allowing any acetone in said sample to interact with said fluorophore; and determining an amount of acetone in said sample based on alteration of spectral properties of said fluorophore, wherein said acetone being detected directly chemically interacts with the fluorophore and any change in said fluorophore spectral properties is from the direct chemical interaction of said acetone with said fluorophore, and wherein the detection does not involve any intermediate chemical reactions of acetone with anything else other than the fluorophore.

2. The method of claim 1, wherein the fluorophores is selected from the group consisting of Nile Red, Badan (6-Bromoacetyl-2-Dimethylaminonaphthalene), Prodan (1-[6-(dimethylamino)naphthalen-2-yl]propan-1-one), Laurdan (6-Dodecanoyl-N,N-dimethyl-2-naphthylamine), and derivatives thereof.

3. The method of claim 1, wherein the fluorophore is immobilized on the surface of a substrate.

4. The method of claim 3, wherein said substrate is selected from the group consisting of fused silica, quartz, PMMA, polyethylene, fluoride-doped polyethylene or PMMA, optical glass and silica gels.

5. The method of claim 1, wherein the alteration of spectral properties is determined by comparing the fluorescence spectrum measured in the presence of the sample with a reference of the fluorescence spectrum shape and intensity.

6. The method of claim 5, wherein the reference is a baseline fluorescence measured prior to obtaining the breath sample.

7. The method of claim 1, determining an amount of acetone in said sample based on alteration of spectral properties of said fluorophore comprises illuminating said fluorophore after combining with said sample, measuring fluorescence and comparing to a reference.

* * * * *